(12) United States Patent
Muto (10) Patent No.: US 9,901,249 B2
(45) Date of Patent: Feb. 27, 2018

(54) TOMOGRAPHIC IMAGE PROCESSING APPARATUS, TOMOGRAPHIC IMAGE PROCESSING METHOD AND PROGRAM

(71) Applicant: CANON KABUSHIKI KAISHA, Tokyo (JP)

(72) Inventor: Kenji Muto, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 34 days.

(21) Appl. No.: 14/659,769

(22) Filed: Mar. 17, 2015

(65) Prior Publication Data

US 2015/0279063 A1    Oct. 1, 2015

(30) Foreign Application Priority Data

Mar. 27, 2014    (JP) ................. 2014-067157

(51) Int. Cl.
*G06K 9/00*    (2006.01)
*A61B 3/12*    (2006.01)
*A61B 3/10*    (2006.01)

(52) U.S. Cl.
CPC ............. *A61B 3/12* (2013.01); *A61B 3/102* (2013.01)

(58) Field of Classification Search
USPC ................................. 382/128–134
See application file for complete search history.

(56) References Cited

U.S. PATENT DOCUMENTS

| | | | |
|---|---|---|---|
| 8,308,297 B2 | 11/2012 | Hirose et al. | |
| 8,390,818 B2 | 3/2013 | Hirose et al. | |
| 8,783,867 B2 | 7/2014 | Muto | |
| 2004/0051710 A1* | 3/2004 | Hara | G06T 19/00 345/419 |
| 2007/0086011 A1* | 4/2007 | Toida | G01N 21/4795 356/450 |
| 2007/0183684 A1* | 8/2007 | Bhattacharjya | G06T 5/008 382/274 |
| 2010/0246917 A1* | 9/2010 | Bruder | A61B 6/032 382/131 |
| 2011/0141259 A1* | 6/2011 | Nakano | A61B 3/0025 348/78 |
| 2012/0249961 A1 | 10/2012 | Muto | |
| 2013/0107213 A1 | 5/2013 | Muto | |

FOREIGN PATENT DOCUMENTS

JP    2008-073099 A    4/2008

\* cited by examiner

*Primary Examiner* — Alex Liew
(74) *Attorney, Agent, or Firm* — Fitzpatrick, Cella, Harper & Scinto (57) ABSTRACT

An ophthalmologic examination apparatus capable of accurately discriminating a boundary between layers indicated by an operator (user) among boundaries of an object to be inspected, when the operator manually changes a position of information designating boundary of layers includes: an acquiring unit configured to acquire a tomographic image of an object to be inspected; a display control unit configured to cause a display unit to display the tomographic image and information designating boundary of layers in the tomographic image; and an adjustment unit configured to adjust, in a case where a boundary of layers is indicated in the displayed information, contrast of the tomographic image such that a brightness difference between layers corresponding to the indicated boundary in the tomographic image becomes large.

22 Claims, 6 Drawing Sheets

TOMOGRAPHIC IMAGE PROCESSING APPARATUS, TOMOGRAPHIC IMAGE PROCESSING METHOD AND PROGRAM

BACKGROUND OF THE INVENTION

Field of the Invention

The present invention relates to a technology for displaying tomographic image data of an object to be inspected.

Description of the Related Art

Recently, apparatuses using Optical Coherence Tomography (OCT) for acquiring tomographic image data by utilizing interference by low coherence light (hereinafter, referred to as an OCT apparatus) are in practical use. The OCT apparatuses can acquire tomographic image data with resolution of a wavelength of light entering an object to be inspected, and therefore can obtain tomographic image data of the object to be inspected with high resolution. Particularly, the OCT apparatuses are useful as ophthalmologic apparatuses for obtaining and displaying tomographic image data of a retina located at an ocular fundus.

Japanese Patent Application Laid-Open No. 2008-73099 discloses a fundus observation apparatus that is configured to obtain a layer position of an ocular fundus, and to superpose the obtained layer position on a cross-sectional image of an ocular fundus to display the superposed image. Furthermore, Japanese Patent Application Laid-Open No. 2008-73099 discloses that in a case where a layer boundary is not clear, accuracy for obtaining the layer position is lowered, and therefore it is convenient to enable an operator to manually change the position of information designating boundary of layers (layer position image) superposed on the cross-sectional image and displayed.

Herein, when the operator manually changes the information designating boundary of layers, the operator needs to accurately discriminate a boundary of layers desired to be manually changed.

SUMMARY OF THE INVENTION

An object of the present invention is to enable an operator (user) to accurately discriminate a boundary of layers indicated by the operator among boundaries of an object to be inspected, when the operator manually changes the position of information designating boundary of layers.

A tomographic image processing apparatus of the present invention has: an acquiring unit configured to acquire a tomographic image of an object to be inspected; a display control unit configured to cause a display unit to display the tomographic image and information designating boundary of layers in the tomographic image; and an adjustment unit configured to adjust, in a case where a boundary of layers is indicated in the displayed information, contrast of the tomographic image such that a brightness difference between layers corresponding to the indicated boundary in the tomographic image becomes large.

According to the present invention, an operator can accurately discriminate a boundary of layers indicated by the operator among boundaries of layers of an object to be inspected, when the operator manually changes the position of information designating boundary of layers.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Below, the present invention is described through embodiments of the invention, but the following embodiments do not limit the claimed invention. Further, all of the combinations of the features described in the embodiments are not limited to the means for solving the problems.

First Embodiment

First, a first embodiment of the present invention is described. A funduscopy apparatus according to the first embodiment displays tomographic image data on a tomographic image display screen, and allows an operator (user) to easily accurately discriminate a boundary of an indicated tomographic image data.

(Configuration of Funduscopy Apparatus)

Figure 1:
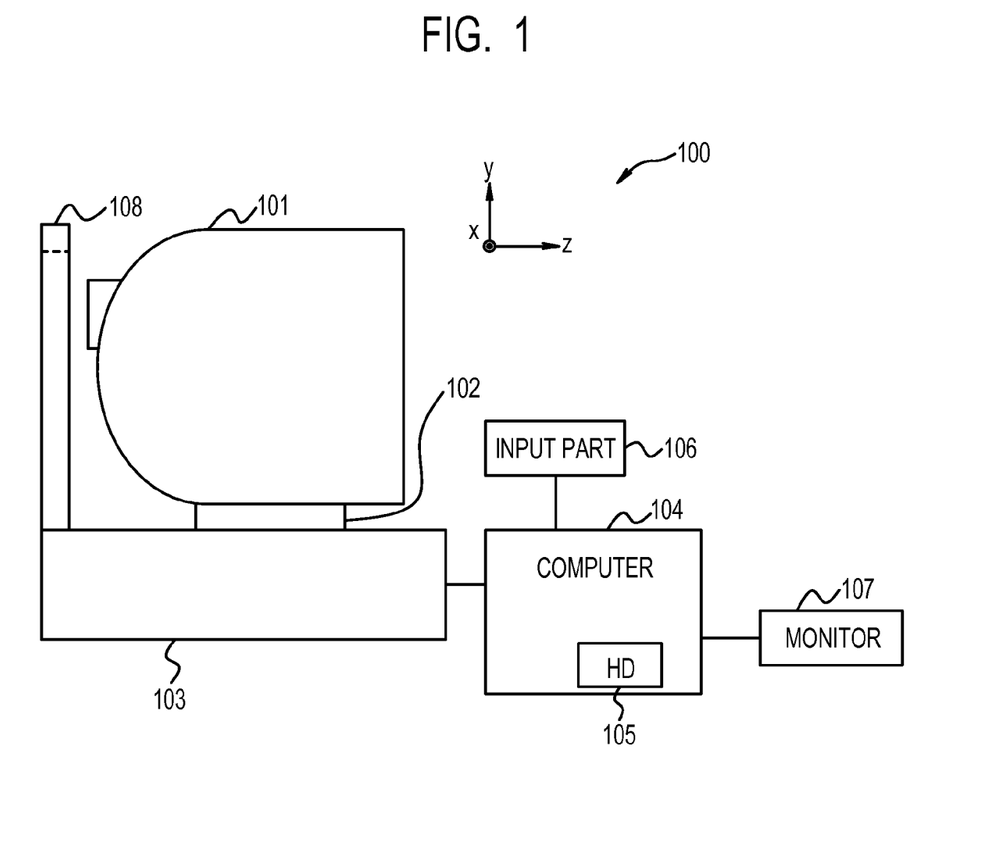
FIG. 1 is a diagram illustrating a configuration of a funduscopy apparatus according to an embodiment of the present invention.

FIG. 1 is a diagram illustrating a configuration of the funduscopy apparatus according to the first embodiment of the present invention. FIG. 1 illustrates an ophthalmologic examination apparatus 100. An optical head part 101 is a measuring optical system for acquiring anterior ocular image data, ocular fundus image data and tomographic image data. A stage part 102 can move the optical head part 101 in the xyz directions of FIG. 1 by using a motor (not illustrated). A base part 103 incorporates a spectroscope described later.

A computer (PC) 104 controls the movement of the stage part 102, and the acquisition of tomographic image data. A hard disk 105 stores examinee information or a program for acquiring tomographic image data. A monitor (display part) 107 displays information thereon. An input part 106 allows a user to instruct the computer 104, and includes a keyboard, a mouse, and the like. A chin rest 108 facilitate the fixing of the eyes of an examinee (eye to be inspected), by fixing the chin and the forehead of the examinee. The computer 104 is an example of a tomographic image processing apparatus for displaying tomographic image data of an object to be inspected.

(Configuration of Measuring Optical System and Spectroscope)

Figure 2:
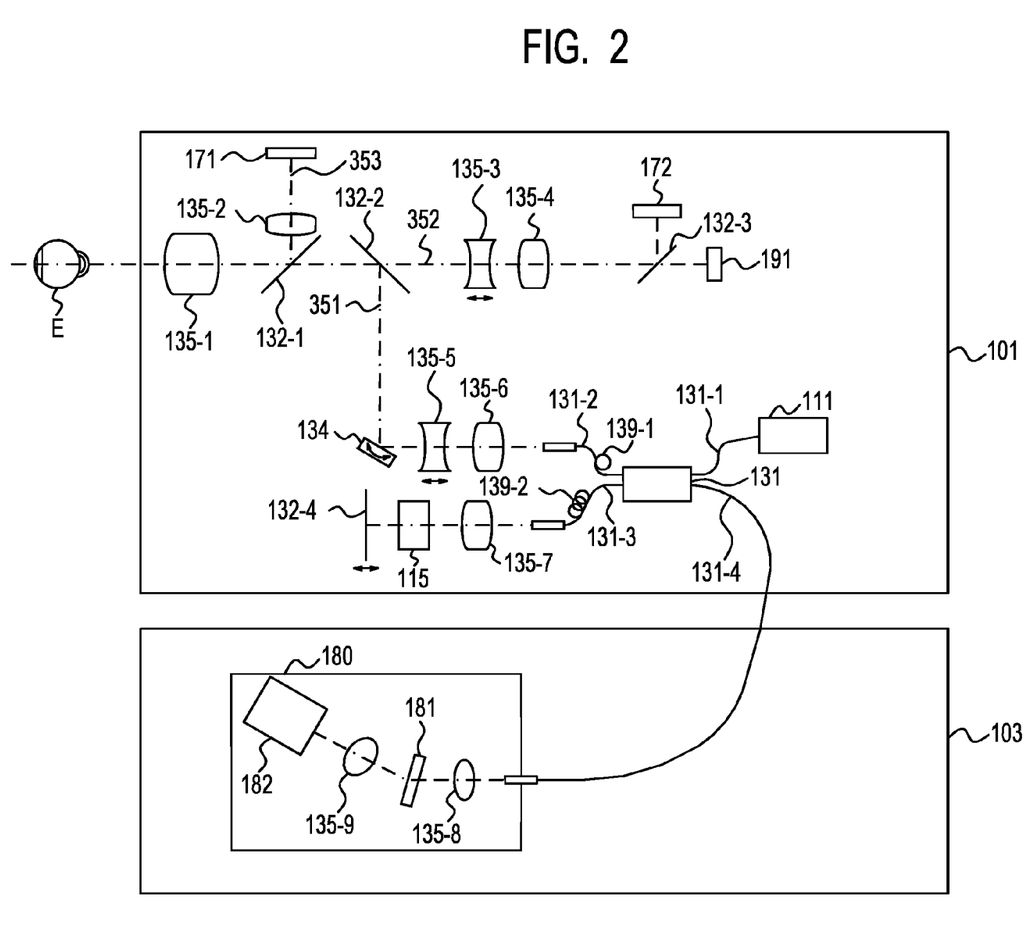
FIG. 2 is a diagram illustrating an internal configuration of an optical head part and a base part.

With reference to FIG. 2, internal configurations of the optical head part 101 and the base part 103 are now described in detail. First, the internal configuration of the optical head part 101 is described. Then, an objective 135-1 is installed so as to face an eye E to be inspected. On an optical axis, an optical path is branched into an optical path 351 of an OCT optical system, an optical path 352 for ocular fundus observation and a fixation lamp unit and an optical path 353 for anterior ocular observation for each wavelength band by a first dichroic mirror 132-1 and a second dichroic mirror 132-2.

Furthermore, the optical path 352 is branched into an optical path to a CCD 172 for ocular fundus observation and an optical path to a fixation lamp unit 191 for each wavelength band by a third dichroic mirror 132-3. Lenses 135-3 and 135-4 are provided. A lens 135-3 is driven by a motor (not illustrated) in order to attain focusing for a fixation lamp unit and ocular fundus observation. The CCD 172 for ocular fundus observation has sensitivity in the neighborhood of the wavelength (780 nm) of illumination light for ocular fundus observation (not illustrated). On the other hand, the fixation lamp unit 191 generates visible light to facilitate the vision fixation of an examinee. In the optical path 353, a lens 135-2 and a CCD 171 for anterior ocular observation are provided. The CCD 171 for anterior ocular observation has sensitivity in the neighborhood of the wavelength (970 nm) of illumination light for anterior ocular observation (not illustrated).

The optical path 351 forms the OCT optical system, and is an optical path for acquiring tomographic image data of the ocular fundus of the eye E to be inspected. More specifically, the optical path 351 is an optical path for obtaining an interference signal for forming tomographic image data. An XY scanner 134 performs scanning on an ocular fundus with light. The XY scanner 134 is illustrated as a single mirror, but performs XY biaxial scanning. Lenses 135-5 and 135-6 are provided. The lens 135-5 is driven by a motor (not illustrated) in order to focus light from a light source 111, emitted from a fiber 131-2 connected to an optical coupler 131, on the ocular fundus of the eye E to be inspected. By this focusing, light from the ocular fundus of the eye E to be inspected is imaged in spot form on the tip of the fiber 131-2 to enter at the same time.

An optical path from the light source 111, a reference optical system and the spectroscope include a mirror 132-4, a dispersion compensation glass 115, and an optical coupler 131, optical fibers 131-1 to 131-4 that are optical fibers of a single mode, each of which is integrally connected to the optical coupler 131, a lens 135-7 and a spectroscope 180.

The above configuration makes up a Michelson interferometer. That is, light emitted from the light source 111 enters the optical coupler 131 through the optical fiber 131-1, and is divided into measuring light on an optical fiber 131-2 side and reference light on an optical fiber 131-3 in the optical coupler 131.

The measuring light is applied to the ocular fundus of the eye E to be inspected through the above OCT optical system optical path, and reaches the optical coupler 131 through the same optical path by reflection or scatter by a retina. On the other hand, the reference light reaches the mirror 132-4 through the optical fiber 131-3, a lens 135-7 and the dispersion compensation glass 115, and then reflected. The dispersion compensation glass 115 is inserted in order to match the dispersion of the measuring light with the reference light. Then, the reference light returns to the same optical path to reach the optical coupler 131.

The measuring light and the reference light are combined by the optical coupler 131 to become interference light. When the optical path length of the measuring light and the optical path length of the reference light become the same, interference occurs. The mirror 132-4 is adjustably held in an optical axis direction by a motor and a drive mechanism (not illustrated), and can match the optical path length of the reference light with the optical path length of the measuring light changed by the eye E to be inspected. The interference light is guided to the spectroscope 180 through an optical fiber 131-4.

A polarization adjustment part 139-1 is provided in the optical fiber 131-2, and is a polarization adjustment part on the measuring light side. A polarization adjustment part 139-2 is provided in the optical fiber 131-3, and is a polarization adjustment part on the reference light side. The polarization adjustment parts 139-1 and 139-2 each have several portions where the optical fiber is wound in a loop shape. These loop shaped portions are rotated with the longitudinal direction of the fiber as the center, and twists are applied to the fiber, so that respective polarization states of the measuring light and the reference light can be adjusted to be matched. In this funduscopy apparatus, the polarization states of the measuring light and the reference light are previously adjusted to be fixed.

The spectroscope 180 includes lenses 135-8 and 135-9, a diffraction grating 181 and a line sensor 182. The interference light emitted from the optical fiber 131-4 becomes parallel light through the lens 135-8, and is thereafter diffracted by the diffraction grating 181 to be imaged in the line sensor 182 by the lens 135-3.

Now, the specification of the light source 111 is described. The light source 111 is an SLD (Super Luminescent Diode) that is a typical low coherent light source. The center wavelength is 855 nm, and the wavelength bandwidth is about 100 nm. The wavelength bandwidth influences resolution in the optical axis direction of obtained tomographic image data, and therefore is an important parameter. As the light source type, the SLD is selected herein, but any light source that emits low coherent light can be employed. For example, an ASE (Amplified Spontaneous Emission) can be employed. In consideration of measurement for eyes, near infrared light is suitable for the center wavelength. Additionally, the center wavelength influences resolution in the horizontal direction of the obtained tomographic image data, and therefore is desired to be a short wavelength as short as possible. In this embodiment, from both these reasons, the center wavelength is set to 855 nm.

In this embodiment, as an interferometer, a Michelson interferometer is used, but a Mach-Zehnder interferometer may be used. In a case where a light quantity difference between the measuring light and the reference light is large, a Mach-Zehnder interferometer is desirably used. In a case where the light quantity difference is relatively small, a Michelson interferometer is desirably used.

(Method for Acquiring Tomographic Image Data)

Now, a method for acquiring tomographic image data using the funduscopy apparatus 100 is described. The funduscopy apparatus 100 can acquire tomographic image data of a desired region in the ocular fundus of the eye E to be inspected by controlling the XY scanner 134.

First, the optical head part 101 performs scanning in the x direction of FIG. 1 with the measuring light, and the line sensor 182 acquires information on a predetermined number of acquisition from an acquiring range in the x direction in the ocular fundus. Image data obtained by applying FFT (fast Fourier transformation) to a brightness distribution on the line sensor 182 obtained at a certain position in the x direction, and converting linear brightness distribution obtained by FFT into concentration or color information in order to display the information on the monitor 107 is referred to as A scan image data. Two-dimensional image data obtained by arranging a plurality of pieces of the A scan image data is referred to as B scan image data. The plurality of pieces of A scan image data are acquired in order to construct a piece of the B scan image data, and a scan position in the y direction is moved to perform scanning in the x direction again, so that a plurality of pieces of the B scan image data are obtained. The plurality of pieces of B scan image data, or three-dimensional tomographic image data constructed from the plurality of pieces of B scan image data is displayed on the monitor 107, so that an operator can use the plurality of pieces of B scan image data, or the three-dimensional tomographic image data for a diagnosis of the eye to be inspected.

(Examination Flow)

Figure 3:
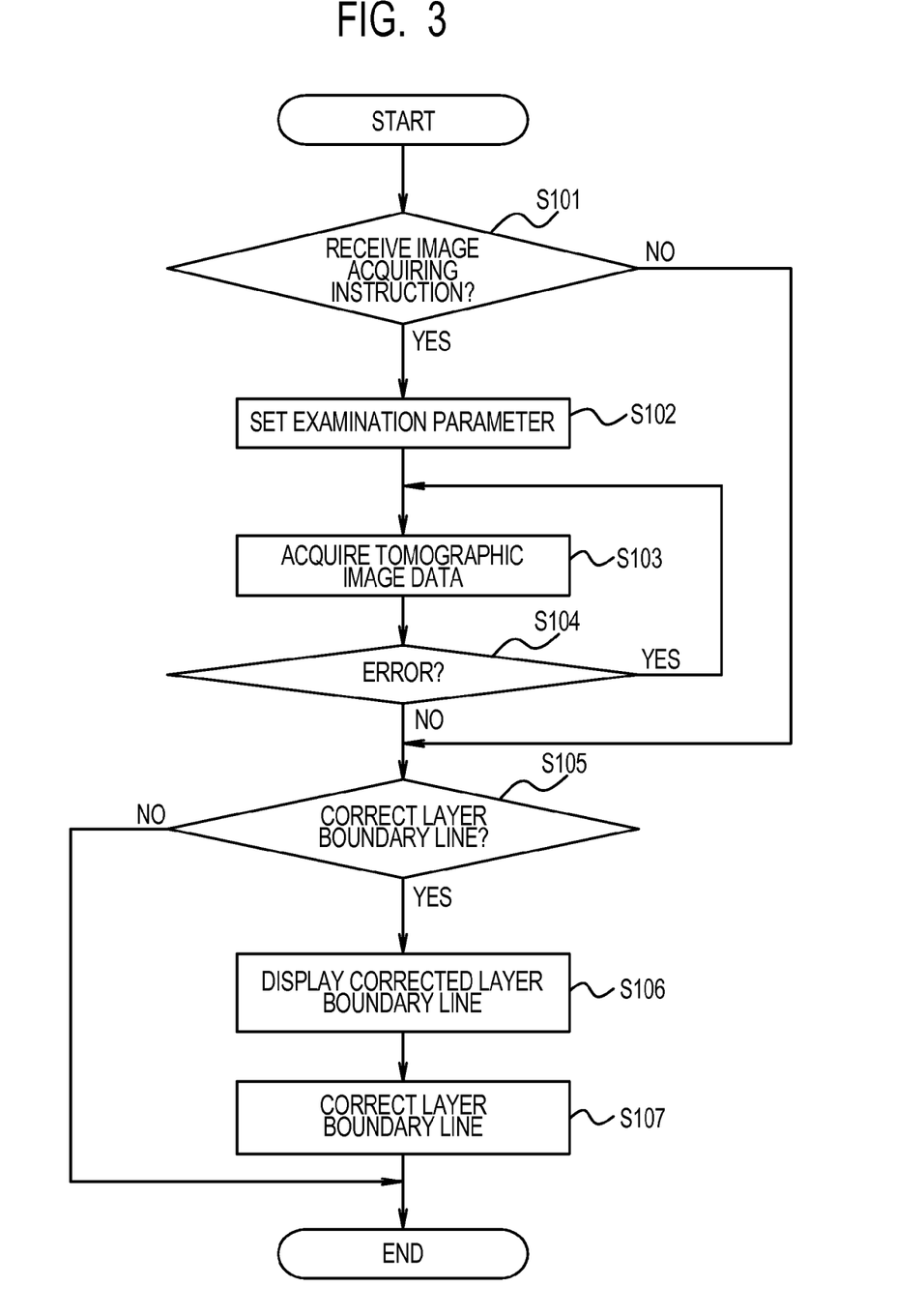
FIG. 3 is a flowchart illustrating a flow of examination processes performed by a computer.

With reference to FIG. 3, a flow of examination processes performed by the computer 104 is now described. The examination processes sometimes proceeds in an order other than the order illustrated in a flowchart of FIG. 3. The processes illustrated in the flowchart of FIG. 3 are processes implemented by causing a CPU (not illustrated) to read a necessary program and data from a recording medium such as a ROM in the computer 104.

When an operator instructs to start an examination, the computer 104 performs a program for acquisition to display a patient information input screen on the monitor 107. In Step S101, the computer 104 determines whether or not an acquisition button is operated, after a patient is selected on the patient information input screen. Herein, the operator selects a patient to be examined on the patient information input screen by operating the input part 106. In a case where the patient to be examined is examined for the first time, information on the patient (such as age, sex and address) is further input. In a case where the operator operates to select the patient to be examined, and thereafter acquires tomographic image data of the eye of the patient, the operator operates the acquisition button on the patient information input screen. Consequently, the process advances to Step S102. On the other hand, when displaying tomographic image data regarding the patient, which has been acquired in the past, the operator operates a past examination display button on the patient information input screen. In this case, the process advances to Step S105.

In Step S102, the computer 104 displays an examination parameter selection screen on the monitor 107. The operator sets "which tomographic image data of right and left eyes to be inspected is displayed", "in which range is tomographic acquisition data acquired", "how many times is tomographic image data acquired", "the number of pieces of the A scan image data included in the B scan image data", and the like as examination parameters on the examination parameter selection screen. Then, the operator operates an OK button displayed on the examination parameter selection screen by using the input part 106. Consequently, the process advances to Step S103.

In Step S103, the computer 104 performs alignment operation of the optical head part 101 to the eye E to be inspected, and thereafter acquires tomographic image data. In Step S104, the computer 104 displays a confirmation screen of the acquired tomographic image data on the monitor 107, and determines whether or not the OK button is operated on the confirmation screen. The operator confirms the acquired tomographic image data by the monitor 107 to determine whether or not an error occurs. In a case where no error occurs, the operator operates the OK button on the confirmation screen by using the input part 106. Consequently, the process advances to Step S105. On the other hand, in a case where the error occurs, the operator operates an NG button on the confirmation screen by using the input part 106. In this case, the process returns to Step S103. In Step S103, the computer 104 functions as an example of an acquiring unit for acquiring tomographic image data of an object to be inspected.

In Step S105, the computer 104 displays an acquired tomographic image data on the tomographic image data confirmation screen, and determines whether or not the necessity of correction of the layer boundary line is input. The tomographic image data displayed in Step S105 is different from the tomographic image data displayed in Step S104. For example, the tomographic image data contains the contents including the layer boundary line by performing a layer analysis by segmentation. In a case where the operator determines that the layer boundary line needs to be corrected, the operator inputs the determined information on the tomographic image data confirmation screen by using the input part 106. Consequently, the process advances to Step S106. On the other hand, in a case where information that the layer boundary line does not need to be corrected is input, the computer 104 ends this examination process. In Step S105, the computer 104 functions as an example of a display control unit for displaying information designating a boundary of layers in tomographic image data.

In Step S106, the computer 104 displays a corrected layer boundary line screen for correcting the layer boundary line, on the monitor 107, and prompts the operator to correct the layer boundary line. The operator instructs to correct the layer boundary line by using the input part 106. In Step S107, the computer 104 corrects the layer boundary line in response to the instruction from the operator. When the correction of the layer boundary line ends, the operator operates an OK button on the corrected layer boundary line screen by using the input part 106. When the computer 104 detects that the OK button is operated, the computer 104 ends the examination process. In Step S106, the computer 104 functions as an example of an adjustment unit for adjusting contrast.

(Tomographic Image Data Display Screen)

Figure 4:
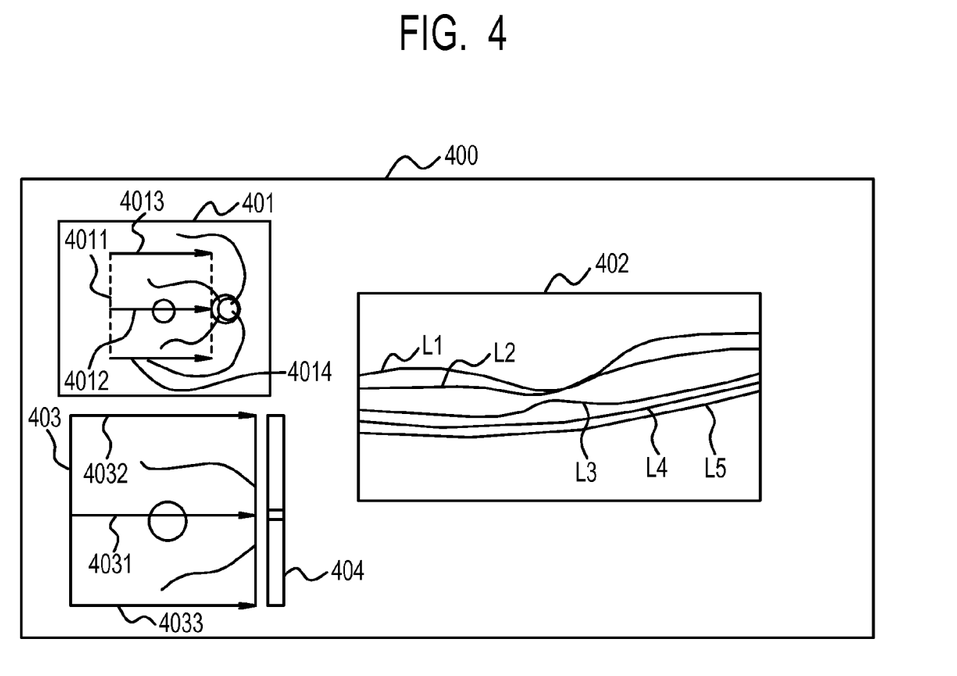
FIG. 4 is a diagram illustrating an example of tomographic image data confirmation screen displayed in Step S105 of FIG. 3.

FIG. 4 is a diagram illustrating an example of a tomographic image data confirmation screen 400 displayed in Step S105. As illustrated in FIG. 4, the tomographic image data confirmation screen 400 includes an ocular fundus image display screen 401, a tomographic image display main screen 402 and a C scan screen 403.

The ocular fundus image display screen 401 is a screen for displaying ocular fundus image data acquired by the CCD 172 for ocular fundus observation. The tomographic image display main screen 402 is a screen for displaying tomographic image data. The C scan screen 403 is a screen for displaying ocular fundus image data equivalent to a range for allowing acquisition of tomographic image data in ocular fundus image data displayed on the ocular fundus image display screen 401 (hereinafter, referred to as a tomographic image acquisition range). A slider 404 is configured to indicate a cross-sectional position of tomographic image data to be displayed on the tomographic image display main screen 402, from the ocular fundus image data displayed on the C scan screen 403.

In the ocular fundus image display screen 401, the tomographic image acquisition range 4011, and the arrows 4012, 4013 and 4014 for illustrating the ranges and the scan directions of tomographic image data displayed on the tomographic image display main screen 402 are illustrated. Similarly, in the C scan screen 403, the arrows 4031, 4032 and 4033 for illustrating the ranges and the scan directions of tomographic image data displayed on the tomographic image display main screen 402 are illustrated.

Layer boundary lines L1 to L5 designated in tomographic image display main screen 402 are segmentation results that are obtained by superposition on tomographic image data, and obtained by the computer 104. These layer boundary lines L1 to L5 are useful for a diagnosis of a state of a retina function, and are very important for the OCT apparatus. For example, the diagnosis of the state of the retina function is performed by measuring the respective thickness of necessary layers in the retina (thicknesses between layer boundary lines), and performing map display (not illustrated) based on the layer boundary lines L1 to L5. Herein, for convenience of description, the five layer boundary lines L1 to L5 are designated. However, a greater number of layer boundary lines for determining the retina function are actually present, about 10 to 11 layer boundary lines are displayed.

In this embodiment, an arbitrary layer boundary line can be selected (indicated) from the layer boundary lines L1 to L5. For example, in a case where the single layer boundary line L2 is selected (indicated) by the operation of clicking with a mouse, or the operation of a selection button (not illustrated), contrast of tomographic image data in the vicinity of the layer boundary line L2 is adjusted. The contrast stated herein is a difference between substantially highest brightness (brightness larger than a threshold value) and substantially lowest brightness (brightness smaller than threshold value) of an image displayed on the tomographic image display screen that is an example of a display unit. Additionally, the brightness stated herein is brightness of a pixel on a display screen of the tomographic image display screen.

Specifically, it is assumed that the layer boundary line L2 is a layer boundary line between a ganglion cell layer (GCL) and an inner plexiform layer (IPL). Generally, in this case, when the contrast is adjusted such that a structure of an entire retina tomogram is easily observed, a brightness difference between the GCL and the IPL is small and a boundary between the GCL and the IPL is considerably difficult to be discriminated. Therefore, in a case where the layer boundary line L2 is selected (indicated), when the contrast is adjusted so as to increase the brightness difference between the GCL and the IPL, an operator easily discriminates whether or not the layer boundary line L2 is accurate by segmentation. Such partial contrast adjustment may be performed to the entire tomographic image display main screen 402, or to a pixel area limited in the vertical direction of the layer boundary line L2, during the selection (indication) of the layer boundary line L2. Herein, the contrast adjustment may be performed such that the brightness difference between the GCL and the IPL is made to be a threshold value or more. This threshold value is not specifically limited, but appropriately set. For example, a user may set a threshold value by using a slider aligned with a tomographic image and displayed on the monitor 107.

Herein, a specific example of the contrast adjustment is described. In a case where an entire tomogram in the vicinity of macula lutea of a certain retina is displayed with a brightness level of 0-255, and a highest brightness part (vicinity of an RPE layer) is displayed with a brightness level of 255 or less, the average brightness value of the IPL is 109, and the average brightness value of a micro area similar to the GCL is 124. In this condition, the brightness difference between the IPL and the GCL is small. Therefore, in a case where the average brightness value of the IPL is made to be 104, and the average brightness value of the GCL is made to 121 by performing contrast adjustment, the discrimination of a layer is facilitated. The above numerical values are just an example.

Figure 5:
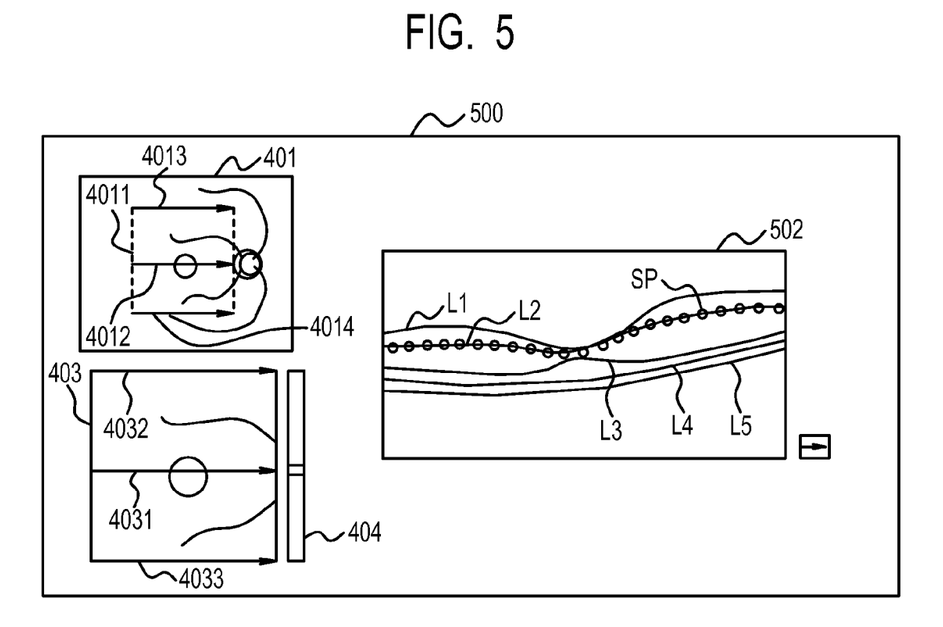
FIG. 5 is a diagram illustrating an example of a corrected layer boundary line screen displayed in Step S106 of FIG. 3.

FIG. 5 is a diagram illustrating an example of a corrected layer boundary line screen 500 displayed in Step S106. As illustrated in FIG. 5, on a tomographic image display main screen 502 of the corrected layer boundary line screen 500, control points SP on a layer boundary line to be corrected are superposed on tomographic image data and a layer boundary line to be displayed. On the tomographic image display main screen 502, the tomographic image data and layer boundary lines are displayed, and a mouse cursor (not illustrated) operated by an operator is superposed on the graphic image data and the layer boundary line to be displayed.

Herein, necessity of the correction of a layer boundary line is described. Tomographic acquired image data by the OCT apparatus sometimes includes a disease such as cataract in the eyes of an examinee, has low SN ratio of the tomographic image data itself, and has low entire contrast. In this case, the discrimination of a boundary between layers by segmentation is not accurately performed, and the correction of a layer boundary line is sometimes necessary.

The operator, for example, shifts the mouse cursor to the layer boundary line L2 to click the mouse cursor, or selects the layer boundary line L2 by the selection button (not illustrated), on the tomographic image display main screen 502, by using the input part 106. Then, the control points SP for correcting a layer boundary line are superposed to be displayed. As illustrated in FIG. 5, a plurality of the control points SP are displayed along the layer boundary line L2. The operator shifts the cursor to a control point SP nearest to a location where the layer boundary line is desired to be corrected, and drags the cursor by operating the mouse, thereby correcting the layer boundary line. A layer boundary line between a control point SP moved at this time and a control point adjacent to the control point SP may be linearly changed, or may be changed to be smoothly connected by a several-order curve. In a tomogram in the vicinity of the selected layer boundary line L2, contrast is partially adjusted to be designed. In a case where the control point SP is moved, the layer boundary line L2 is changed, and segmentation itself is changed. Therefore, the contrast may be readjusted based on a newly prescribed area, and the tomographic image data may be redisplayed. Consequently, it is possible to emphasize a brightness difference between layers in the tomographic image data, and to easily recognize a position to which the control point SP is moved by the operator.

Second Embodiment

Now, a second embodiment of the present invention is described. The second embodiment is different from the first embodiment in a process in Step S106 of FIG. 3, but is similar to the first embodiment in other processes and configurations. Therefore, description of the similar process and configurations is omitted.

Figure 6:
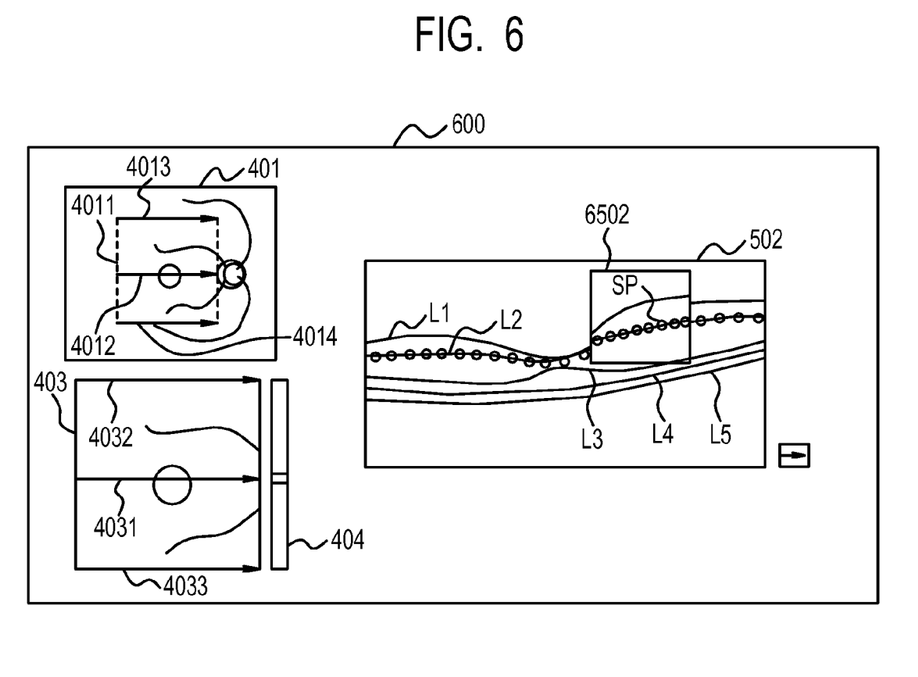
FIG. 6 is a diagram illustrating an example of a corrected layer boundary line screen displayed in Step S106 of a second embodiment.

FIG. 6 is a diagram illustrating an example of a corrected layer boundary line screen 600 displayed in Step S106 of the second embodiment. As illustrated in FIG. 6, in the second embodiment, a computer 104 functions as an example of a display control unit, and displays an enlarged screen 6502 in the vicinity of a control point SP to be corrected, on a corrected layer boundary line screen 600. This enlarged screen 6502 is displayed when an operator moves a cursor to a position near the control point SP desired to be corrected (enlarged position) by operating a mouse. In the enlarged screen 6502, an enlarged area in tomographic image data corresponding to the above enlarged position is enlarged and displayed with a display magnification of 2, and the number of the control points SP is increased twofold compared to the number of the control points SP in the tomographic image display main screen 502, thereby enabling fine correction. The display magnification and the rate of increase in the number of the control points SP, described above, each are just an example. Additionally, the operator performs click operation of the mouse in the enlarged screen 6502 once, so that tomographic image data displayed in the enlarged screen 6502 is fixed. Accordingly, in this state, the operator can move the control point SP by drag operation with the mouse. After this movement operation of the control point SP ends, the operator performs click operation of the mouse in the enlarged screen 6502 once, so that it is possible to move the tomographic image data displayed in the enlarged screen 6502, and to select an area to be corrected.

In the enlarged screen 6502, the operator can easily recognize a position to which the control point SP is moved, by contrast adjustment in the enlarged screen 6502, and emphasis of a brightness difference in the enlarged screen 6502. Additionally, the number of the control points in the enlarged screen 6502 is made larger than the number of the control points tomographic image display main screen 502 outside the enlarged screen 6502, thereby enabling fine correction.

Furthermore, in the contrast adjustment in the enlarged screen 6502, partial contrast adjustment may be added to a tomogram in the vicinity of a selected layer boundary line L2, similarly to the first embodiment.

As described above, in the above embodiments, an operator easily accurately discriminates a layer boundary, thereby facilitating the correction of the layer boundary. Additionally, in the above embodiments, a layer boundary watched by the operator can be accurately discriminated in display of tomographic image data. Therefore, examination itself is simplified, and accurate determination regarding the examination can be facilitated.

Additionally, the present invention is implemented by performing the following processes. That is, in the processes, software (program) implemented by the functions of the above embodiments is supplied to a system or an apparatus through a network or various storage media, and a computer (or CPU, MPU) of the system or the apparatus reads and performs the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-067157, filed Mar. 27, 2014, which is hereby incorporated by reference herein in its entirety.

What is claimed is:

1. A tomographic image processing apparatus comprising:
    an analyzing unit configured to perform layer analysis of a tomographic image of an eye to be inspected, the tomographic image having been obtained using an OCT (Optical Coherence Tomography) optical system;
    a display control unit configured to cause a display unit to display (1) the tomographic image and (2) information indicating a plurality of boundaries of layers in the tomographic image; and
    an adjustment unit configured to adjust, in a case where a boundary of layers is selected from the indicated plurality of boundaries, contrast of the tomographic image such that (a) a brightness difference between layers corresponding to the selected boundary in the tomographic image becomes larger and (b) a brightness of a layer different from the layers corresponding to the selected boundary is maintained.

2. The tomographic image processing apparatus according to claim 1, wherein the adjustment unit adjusts the contrast of the tomographic image such that the brightness difference between the layers is a threshold value or more.

3. The tomographic image processing apparatus according to claim 1, wherein, in a case where the information indicating the plurality of boundaries of layers is operated so as to move the boundary between the layers, the adjustment unit adjusts contrast of an area of the tomographic image corresponding to boundary of layers obtained after the operation.

4. The tomographic image processing apparatus according to claim 1, wherein in a case where an enlarged position is selected from the tomographic image, the display control unit causes the display unit to enlarge and display an area of the tomographic image corresponding to the selected enlarged position.

5. The tomographic image processing apparatus according to claim 1, wherein the display control unit (a) causes the display unit to display a cursor operated by a user, and a control point for controlling the information indicating the plurality of boundaries of layers that are superimposed on the tomographic image, (b) causes the display unit to enlarge and display an area of the tomographic image corresponding to a position to which the cursor is shifted, and (c) increases the number of the control points in the enlarged and displayed area.

6. The tomographic image processing apparatus according to claim 4, wherein the adjustment unit adjusts contrast of an area of the tomographic image corresponding to the selected enlarged position.

7. The tomographic image processing apparatus according to claim 1, wherein the display control unit causes the display unit to display a cursor operated by a user, the cursor being superimposed on the tomographic image and the information indicating a plurality of boundaries of layers in the tomographic image, and causes the display unit to enlarge and display an area of the tomographic image corresponding to a position to which the cursor is shifted, and
    wherein the adjustment unit adjusts contrast of the enlarged and displayed area.

8. The tomographic image processing apparatus according to claim 1, wherein the tomographic image processing apparatus controls a stage unit that drives an optical head including (a) an optical path used for acquiring an anterior ocular segment observation image of the eye to be inspected, (b) an optical path used for acquiring a fundus observation image of the eye to be inspected, and (c) an optical path of the OCT optical system.

9. A tomographic image processing method performed by a tomographic image processing apparatus, the tomographic image processing method comprising:
    performing layer analysis of a tomographic image of an eye to be inspected, the tomographic image having been obtained using an OCT (Optical Coherence Tomography) optical system;
    causing a display unit to display the tomographic image and information indicating a plurality of boundaries of layers in the tomographic image;
    adjusting, in a case where a boundary of layers is selected from the indicated plurality of boundaries, contrast of the tomographic image such that (a) a brightness difference between layers corresponding to the selected boundary in the tomographic image becomes larger and (b) a brightness of a layer different from the layers corresponding to the selected boundary is maintained.

10. The tomographic image processing method according to claim 9, wherein in the adjustment, the contrast of the tomographic image is adjusted such that the brightness difference between the layers of the tomographic image corresponding to the selected boundary is a threshold value or more.

11. The tomographic image processing method according to claim 9, wherein in the adjustment, in a case where the information indicating a plurality of boundaries of layers is operated so as to move the boundary between the layers, contrast of an area of the tomographic image corresponding to the boundary of layers obtained after the operation is adjusted.

12. The tomographic image processing method according to claim 9, wherein in the adjustment, in a case where an enlarged position is selected from the tomographic image, an area of the tomographic image corresponding to the selected enlarged position is enlarged and displayed.

13. The tomographic image processing method according to claim 9, wherein in the display, (a) a cursor operated by a user and a control point for controlling the information indicating a plurality of boundaries of layers are superimposed on the tomographic image, (b) an area of the tomographic image corresponding to a position to which the cursor is shifted is enlarged and displayed, and (c) the number of the control points in the enlarged displayed area is increased.

14. The tomographic image processing method according to claim 12, wherein in the adjustment, contrast of an area of the tomographic image corresponding to the selected enlarged position is adjusted.

15. The tomographic image processing method according to claim 9, wherein in the display, a cursor operated by a user is superimposed on the tomographic image and the information indicating a plurality of boundaries of layers in the tomographic image to be displayed, and an area of the tomographic image corresponding to a position to which the cursor is shifted is enlarged and displayed, and
wherein in the adjustment, contrast of the enlarged and displayed area is adjusted.

16. The tomographic image processing method according to claim 9, wherein the tomographic image processing apparatus controls a stage unit that drives an optical head including (a) an optical path used for acquiring an anterior ocular segment observation image of the eye to be inspected, (b) an optical path used for acquiring a fundus observation image of the eye to be inspected, and (c) an optical path of the OCT optical system.

17. A non-transitory tangible medium having recorded thereon a program for causing a computer to perform steps of the tomographic image processing method according to claim 9.

18. The tomographic image processing apparatus according to claim 1, wherein the OCT optical system is configured to acquire the tomographic image of the eye to be inspected by using a combined light obtained by combining (a) a return light from the eye illuminated with a measuring light, with (b) a reference light corresponding to the measuring light, and
wherein the OCT optical system comprises a drive mechanism configured to adjust the optical path difference between an optical path length of the measuring light and an optical path length of the reference light.

19. A tomographic image processing apparatus, comprising:
an analyzing unit configured to perform layer analysis of a tomographic image of an eye to be inspected, the tomographic image having been obtained using an OCT (Optical Coherence Tomography) optical system;
a display control unit configured to cause a display unit to display (1) the tomographic image and (2) information indicating a plurality of boundaries of layers in the tomographic image; and
an adjustment unit configured to adjust, in a case where a boundary of layers is selected from the indicated plurality of boundaries, contrast of the tomographic image such that (a) a brightness difference between layers corresponding to the selected boundary in the tomographic image becomes larger and (b) a brightness of a layer different from the layers corresponding to the selected boundary is maintained,
wherein the OCT optical system is configured to acquire the tomographic image of the eye to be inspected by using a combined light obtained by combining (a) a return light from the eye illuminated with a measuring light, with (b) a reference light corresponding to the measuring light, and
wherein the OCT optical system comprises (a) a drive mechanism configured to adjust the optical path difference between an optical path length of the measuring light and an optical path length of the reference light, (b) a XY scanner which scans with the measuring light on a fundus of the eye to be inspected, (c) a dispersion compensation glass which is provided on the optical path of the reference light, (d) an optical fiber which is provided on the optical path of the reference light, and (e) a polarization adjustment part provided on the optical fiber.

20. The tomographic image processing apparatus according to claim 1, wherein the display control unit causes the display unit to superimpose the information about the plurality of boundaries on the tomographic image.

21. The tomographic image processing apparatus according to claim 20, wherein the boundary of layers is selected by designating one of the plurality of boundaries indicated by the displayed information.

22. The tomographic image processing apparatus according to claim 1, wherein the adjustment unit makes the brightness difference between layers larger by changing the brightness of layers corresponding to the selected boundary.

* * * * *